United States Patent
Meyer-Ahrens et al.

(10) Patent No.: US 10,563,032 B2
(45) Date of Patent: Feb. 18, 2020

(54) METHOD FOR PRODUCING FLAME RETARDANT POLYURETHANE FOAMS USING HALOGEN-FREE FLAME RETARDANTS

(71) Applicant: Covestro Deutschland AG, Leverkusen (DE)

(72) Inventors: Sven Meyer-Ahrens, Leverkusen (DE); Stephan Reiter, Langenfeld (DE); Engin Cavlan, Köln (DE); Matthäus Gossner, Köln (DE)

(73) Assignee: Covestro Deutschland AG, Leverkusen (DE)

( * ) Notice: Subject to any disclaimer, the term of this patent is extended or adjusted under 35 U.S.C. 154(b) by 57 days.

(21) Appl. No.: 15/525,968

(22) PCT Filed: Nov. 18, 2015

(86) PCT No.: PCT/EP2015/076955
§ 371 (c)(1),
(2) Date: May 11, 2017

(87) PCT Pub. No.: WO2016/079175
PCT Pub. Date: May 26, 2016

(65) Prior Publication Data
US 2017/0306122 A1   Oct. 26, 2017

(30) Foreign Application Priority Data

Nov. 18, 2014   (EP) .................... 14193606

(51) Int. Cl.
| | |
|---|---|
| *C08G 18/48* | (2006.01) |
| *C08J 9/00* | (2006.01) |
| *C08G 18/76* | (2006.01) |
| *C08K 5/523* | (2006.01) |
| *C07F 9/12* | (2006.01) |
| *C09K 21/12* | (2006.01) |
| *C08G 101/00* | (2006.01) |

(52) U.S. Cl.
CPC .............. *C08J 9/0038* (2013.01); *C07F 9/12* (2013.01); *C08G 18/4837* (2013.01); *C08G 18/7621* (2013.01); *C08K 5/523* (2013.01); *C09K 21/12* (2013.01); *C08G 2101/005* (2013.01); *C08G 2101/0008* (2013.01); *C08G 2101/0083* (2013.01); *C08J 2205/06* (2013.01); *C08J 2375/04* (2013.01)

(58) Field of Classification Search
CPC ... C07F 9/12; C08G 18/4837; C08G 18/4866; C08G 18/7621; C08G 2101/00; C08G 2101/0008; C08G 2101/005; C08G 2101/0083; C08J 9/0038; C08J 2205/06; C08J 2375/04; C08K 5/0066; C08K 5/523; C09K 21/12; C08L 75/04

See application file for complete search history.

(56) References Cited

U.S. PATENT DOCUMENTS

| | | |
|---|---|---|
| 4,248,930 A | 2/1981 | Haas et al. |
| 4,263,408 A | 4/1981 | Meyborg et al. |
| 4,777,189 A | 10/1988 | Shimomura et al. |
| 6,242,631 B1 | 6/2001 | Hombek et al. |
| 2006/0116432 A1 | 6/2006 | Phillips et al. |
| 2007/0112084 A1 | 5/2007 | Hansel et al. |
| 2010/0041780 A1* | 2/2010 | Friedrich .............. C08G 18/10 521/107 |
| 2014/0179811 A1 | 6/2014 | Layman, Jr. et al. |

FOREIGN PATENT DOCUMENTS

| | | |
|---|---|---|
| CA | 1337448 | 10/1995 |
| EP | 0176013 A2 | 4/1986 |
| EP | 1857586 A1 | 11/2007 |

OTHER PUBLICATIONS

Oertel, Gunter; Polyurethane Handbook, 2nd Edition; Hanser Publishing, NY (1993); pp. 98-119 believed to correspond to Kunststoff Handbuch; vol. VII, pp. 104-127, edited by G. Oertel, Carl Hanser-Verlag, Munich, 3rd edition, (1993).

Oertel, Gunter; Polyurethane Handbook, 2nd Edition; Hanser Publishing, NY (1993); pp. 129-245; believed to correspond to Kunststoff Handbuch; vol. VII, pp. 139-265, edited by Vieweg and Hochtlen, Carl-Hanser-Verlag, Munich, (1993).

Kunihiko Takeda et al., Flame Retardancy and Rearrangement Reaction of Polyphenylene-ether / Polystyrene Alloy; Journal of Applied Polymer Science, vol. 64(6), pp. 1175-1183.

* cited by examiner

Primary Examiner — John M Cooney
(74) Attorney, Agent, or Firm — N. Denise Brown

(57) ABSTRACT

The present invention relates to a process for producing flame-retarded polyurethane foams, in particular flexible polyurethane foams, using halogen-free flame retardants, wherein the resulting flame-retarded polyurethane foams exhibit low emission values coupled with good mechanical properties. The present invention further relates to halogen-free flame retardants.

4 Claims, No Drawings

METHOD FOR PRODUCING FLAME RETARDANT POLYURETHANE FOAMS USING HALOGEN-FREE FLAME RETARDANTS

CROSS-REFERENCE TO RELATED APPLICATIONS

This Application is a national stage application under 35 U.S.C. § 371 of PCT/EP2015/076955, filed Nov. 18, 2015, which claims the benefit of EP Application No. 14193606.2, filed Nov. 18, 2014, both of which are incorporated by reference herein.

FIELD

The present invention relates to a process for producing flame-retarded polyurethane foams, in particular flexible polyurethane foams, using halogen-free flame retardants, wherein the resulting flame-retarded polyurethane foams exhibit low emission values coupled with good mechanical properties. The present invention further relates to halogen-free flame retardants.

BACKGROUND

A great many different flame retardants are known from the prior art and commercially available. Halogen-containing alkyl phosphates, for example tris(chlorethyl) phosphate, tris(chlorisopropyl) phosphate and tris(2,3-dichloroisopropyl) phosphate are often employed as flame retardants in the production of flame-retarded flexible polyurethane foams. These halogen-containing flame retardants are receiving increasing criticism from polyurethane (PUR) processors and end-users and the halogen content in the end product is in some cases limited by third-party certification marks (product labels). The abovementioned flame retardants also lead to increased emission values for the resulting polyurethane foams.

Furthermore, halogen-free flame retardants that may be employed in polyurethane foams include alkyl phosphates (e.g. triethyl phosphate), aryl phosphates (e.g. diphenyl cresyl phosphate) and alkyl phosphonates (e.g. dimethylpropane phosphonate). These compounds are liquid and thus exhibit good processability in the production of the polyurethane foam but due to their relatively low molecular weights they also have a relatively high volatility which has a negative effect on the emission values of the resulting polyurethane foams.

For special applications such as the use of polyurethane foams in automobile interiors for example it is a requirement that emissions of volatile organic compounds (VOC) and/or condensable emissions (fogging) from these polyurethane foams shall not exceed low threshold values.

Fogging refers to the undesired condensation of evaporated volatile constituents from the motor vehicle interior on glass panes, in particular on the windscreen. This phenomenon is quantifiable as per DIN 75 201. The automotive industry typically requires that the fogging condensate as determined by the DIN 75 201 B method may be less than 1 mg.

Also known are the so-called "reactive flame retardants" which bear isocyanate-reactive hydroxyl groups and thus react with the polyisocyanate employed for foam production and are incorporated into the polyurethane. These foams therefore show only small VOC and fogging contributions. These include both halogen-containing and halogen-free phosphorous flame retardants. However, due to their (OH)-functionality said flame retardants in some cases exhibit considerable problems during foam production since they increase the crosslinking density of the PUR matrix. Mechanical properties and/or the processability of the liquid components to afford the finished foam are adversely affected so that the reactive flame retardants can be used in the formulation only to a limited extent.

Also prior art are solid, usually halogen-free flame retardants such as melamine, aluminum or magnesium oxide or ammonium polyphosphates. Solid flame retardants necessitate special metering devices, have a deleterious effect on foam properties and considerably increase the viscosity of the reaction mixture which may in turn result in undesired air inclusions and flow lines in the foam.

EP-A 0170206 discloses a process for producing flame-retarded polyurethane foams. Triaryl phosphate esters are disclosed as suitable flame retardants. The resulting polyurethane foams show a low level of skin staining.

EP-A 1785439 discloses 2-hydroxyalkanephosphonates and/or 3-hydroxyalkanephosphonates as halogen-free flame retardants in polyurethane foams. No information about the mechanical properties of the resulting polyurethanes is provided. However, it is pointed out that the reactive monofunctional flame retardants too are afflicted by the fundamental disadvantages of the reactive flame retardants, albeit in attenuated form. It is known to one skilled in the art that monofunctional additives bring about chain termination in the PUR network and therefore (likewise) compromise the mechanical properties of the resulting foam.

US-A 2014/0179811 discloses the use of mixed-C1-C5-alkylated triaryl phosphates having not more than two unsubstituted phenyl radicals and comprising less than 1 wt % of triphenylphosphine based on the total amount of employed alkylated triaryl phosphates for producing flame-retarded polyurethane or polyisocyanurate foams. US-A 2014/0179811 does not disclose any teaching regarding the volatility of the described flame retardants or the polyurethanes produced therewith. On the contrary, the aim is to avoid triphenyl phosphate which in the specification is said to have deleterious environmental properties.

The constantly increasing requirements of low-emissions polyurethane foams, in particular of flexible polyurethane foams, in special applications such as in automobile interiors for example make it necessary to use special halogen-free flame retardants in the production of polyurethane foams.

SUMMARY OF THE INVENTION

The present invention accordingly has for its object to provide a process for producing flame-retarded polyurethane foams, in particular flexible polyurethane foams, using halogen-free flame retardants, wherein the resulting polyurethane foams exhibit low fogging values according to DIN 75201 B. The total emission according to VDA 278, in which the sum of high-volatility substances (VOC value) and of the relatively low-volatility substances (FOG value) is determined, should likewise be low in the resulting PUR foams.

This object is achieved by a process for producing polyurethane foams by reaction of a component comprising
   a) at least one compound which comprises isocyanate-reactive hydrogen atoms,
   b) water and/or physical blowing agent,
   c) auxiliary and additive substances,
   d) at least one halogen-free flame retardant comprising
     d.1) a phosphoric ester of formula (I)

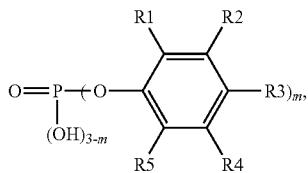

(I)

in which m is an integer from 1 to 3, $R_1$, $R_2$, $R_3$, $R_4$, $R_5$ each independently represent H, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, and/or $COOR_{11}$ where $R_{11}=C_1$- to $C_5$-alkyl radical, preferably $C_1$- to $C_3$-alkyl radical, particularly preferably $C_1$-alkyl radical, and wherein at least one of the radicals $R_1$, $R_2$, $R_3$, $R_4$, $R_5$ is distinct from H, or d.2) a phosphoric ester of formula (II)

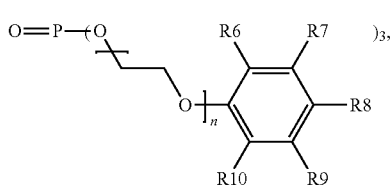

(II)

in which n represents an integer from 1 to 4, preferably from 1 to 2, particularly preferably of 1, $R_6$, $R_7$, $R_8$, $R_9$, $R_{10}$ each independently represent H, a straight-chain, branched or cyclic $C_1$- to $C_{10}$-alkyl radical, preferably $C_1$- to $C_6$-alkyl radical, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, and/or $COOR_{11}$ where $R_{11}=C_1$- to $C_5$-alkyl radical, preferably $C_1$- to $C_3$-alkyl radical, particularly preferably $C_1$-alkyl radical, with e) at least one di- and/or polyisocyanate, wherein the mixture is free from halogen-containing flame retardants.

In one embodiment of the process component a) is employed in an amount of 100 parts by wt, component b) is employed in an amount of 0.5 to 25 parts by wt (per 100 parts by wt of a) (=parts per hundred parts: pphp)), component c) is employed in an amount of 0.05 to 10 pphp and component d) is employed in an amount of 1 to 30 pphp.

The present application further provides flame retardants comprising d.1) a phosphoric ester of formula (I)

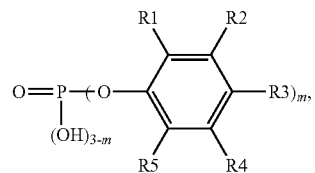

(I)

in which m is an integer from 1 to 3, $R_1$, $R_2$, $R_3$, $R_4$, $R_5$ each independently represent H, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, and/or $COOR_{11}$ where $R_{11}=C_1$- to $C_5$-alkyl radical, preferably $C_1$- to $C_3$-alkyl radical, particularly preferably $C_1$-alkyl radical, and wherein at least one of the radicals $R_1$, $R_2$, $R_3$, $R_4$, $R_5$ is distinct from H, or d.2) a phosphoric ester of formula (II)

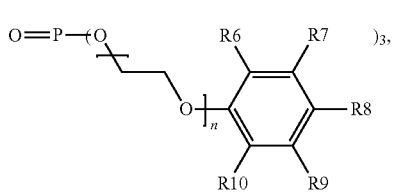

(II)

in which n represents an integer from 1 to 4, preferably from 1 to 2, particularly preferably of 1, $R_6$, $R_7$, $R_8$, $R_9$, $R_{10}$ each independently represent H, a straight-chain, branched or cyclic $C_1$- to $C_{10}$-alkyl radical, preferably $C_1$- to $C_6$-alkyl radical, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, and/or $COOR_{11}$ where $R_{11}=C_1$- to $C_5$-alkyl radical, preferably $C_1$- to $C_3$-alkyl radical, particularly preferably $C_1$-alkyl radical,

DETAILED DESCRIPTION

To produce the polyurethane foams, the reaction components are reacted by the one-step process known per se, often using mechanical means, for example those described in EP-A 355 000. Details of processing means also contemplated in accordance with the invention are reported in Kunststoff-Handbuch, volume VII, edited by Vieweg and Höchtlen, Carl-Hanser-Verlag, Munich 1993, for example on pages 139 to 265.

The polyurethane foams are preferably in the form of flexible polyurethane foams and may be produced as molded foams or else as slabstock foams, preferably as slabstock foams. The invention therefore provides a process for producing the flame-retarded polyurethane foams, the flame-retarded polyurethane foams produced by these processes, the flame-retarded flexible polyurethane slabstock foams and flame-retarded flexible polyurethane molded foams produced by these processes, and also for the use of the flame-retarded flexible polyurethane foams.

The components employed in the process according to the invention are more particularly described hereinbelow.

Component a)

Compounds according to component a) are compounds comprising isocyanate-reactive hydrogen atoms having a hydroxyl number (OH number) according to DIN 53240 of ≥5 mg KOH/g to ≤250 mg KOH/g, preferably of ≥9 mg KOH/g to ≤112 mg KOH/g, particularly preferably of ≥28 mg KOH/g to ≤60 mg KOH/g.

Production of the compounds according to component a) is effected in a manner known per se by addition of alkylene oxides onto starter compounds having isocyanate-reactive hydrogen atoms under base catalysis or by using double metal cyanide compounds (DMC compounds). The starter compounds usually have functionalities of 2 to 8, preferably of 2 to 6, particularly preferably of 3, and are preferably hydroxy-functional. Examples of hydroxy-functional starter compounds are propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-dodecanediol, glycerol, trimethylolpropane, triethanolamine, pentaerythritol, sorbitol, sucrose, hydroquinone, catechol, resorcinol, bisphenol F, bisphenol A, 1,3,5-trihydroxybenzene, methylol-containing condensates of formaldehyde and phenol or melamine or urea. Preferably employed starter compounds are glycerol and/or trimethylolpropane.

Suitable alkylene oxides are, for example, ethylene oxide, propylene oxide, 1,2-butylene oxide/2,3-butylene oxide and styrene oxide. It is preferable when propylene oxide and ethylene oxide are supplied to the reaction mixture individually, in admixture or successively. When the alkylene oxides are metered in successively the products produced (polyether polyols) comprise polyether chains having block structures. Products having ethylene oxide end blocks are characterized, for example, by elevated concentrations of primary end groups which impart advantageous isocyanate reactivity to the systems.

The functionality of the polyether polyols is determined by the functionality of the starting compounds employed for producing the polyether polyols.

In one embodiment of the invention component a) has a hydroxyl number (OH number) according to DIN 53240 of ≥5 mg KOH/g to ≤250 mg KOH/g, preferably of ≥9 mg KOH/g to ≤112 mg KOH/g, particularly preferably of ≥28 mg KOH/g to ≤60 mg KOH/g, a hydroxyl functionality of 2 to 8, preferably of 2 to 6, particularly preferably of 2 to 3. It is preferable when propylene oxide and/or ethylene oxide are supplied individually, in admixture or successively in the addition reaction of alkylene oxide onto suitable starter compounds.

In a preferred embodiment component a) has an OH number according to DIN 53240 of ≥28 mg KOH/g to ≤60 mg KOH/g, a hydroxyl functionality of 2 to 3 and a proportion of ≥75 wt %, preferably ≥85 wt %, particularly preferably ≥95 wt %, of propylene oxide.

Component b)

Water and/or physical blowing agents are employed as component b). Physical blowing agents employed as blowing agents are for example carbon dioxide and/or volatile organic substances.

Component c)

Used as component c) are auxiliary and additive substances such as c.1) catalysts (activators),
c.2) surface-active additive substances (surfactants), such as emulsifiers and customary foam stabilizers
c.3) additives such as reaction retardants (for example acidic substances such as hydrochloric acid or organic acyl halides), cell regulators (for example paraffins or fatty alcohols or dimethylpolysiloxanes), pigments, dyes, optionally further flame retardants, stabilizers against aging and weathering effects, plasticizers, fungistatic and bacteriostatic substances, fillers (for example barium sulfate, kieselguhr, carbon black or whiting) and separating agents.

These auxiliary and added substances for optional use are described for example in EP-A 0 000 389, pages 18-21. Further examples of auxiliary and added substances for optional use according to the invention and also details concerning ways these auxiliary and added substances are used and function are described in Kunststoff-Handbuch, volume VII, edited by G. Oertel, Carl-Hanser-Verlag, Munich, 3rd edition, 1993, for example on pages 104-127.

Preferred as catalysts are aliphatic tertiary amines (for example trimethylamine, tetramethylbutanediamine), cycloaliphatic tertiary amines (for example 1,4-diaza[2.2.2]bicyclooctane, aliphatic amino ethers (for example dimethylaminoethyl ether and N,N,N-trimethyl-N-hydroxyethyl-bisaminoethyl ether), cycloaliphatic amino ethers (for example N-ethylmorpholine), aliphatic amidines, cycloaliphatic amidines, urea, derivatives of urea (for example aminoalkylureas; see, for example, EP-A 0 176 013, especially (3-dimethylaminopropylamino)urea), and tin catalysts (for example dibutyltin oxide, dibutyltin dilaurate, tin octoate).

Particularly preferred as catalysts c.1) are c.1.1) urea, derivatives of urea and/or
c.1.2) tin catalysts, preferably dibutyltin oxide, dibutyltin dilaurate, tin octoate, particularly preferably tin octoate and/or
c.1.3) tertiary amines (for example 1,4-diaza(2,2,2)bicyclooctane), aliphatic amino ethers (for example dimethylamino ethyl ether).

Component d)

Employed in accordance with the invention is at least one halogen-free flame retardant comprising d.1) a phosphoric ester of formula (I)

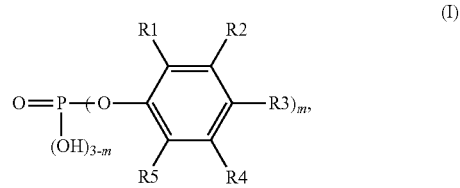

in which m represents an integer from 1 to 3,
$R_1$, $R_2$, $R_3$, $R_4$, $R_5$ each independently represent H, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, and/or $COOR_{11}$ where $R_{11}=C_1$- to $C_5$-alkyl radical, preferably $C_1$- to $C_3$-alkyl radical, particularly preferably $C_1$-alkyl radical, and wherein at least one of the radicals $R_1$, $R_2$, $R_3$, $R_4$, $R_5$ is distinct from H, or d.2) a phosphoric ester of formula (II)

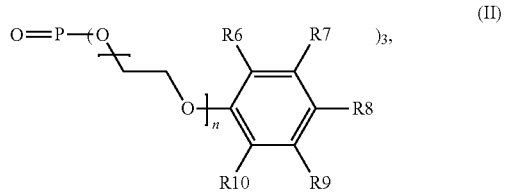

in which n represents an integer from 1 to 4, preferably from 1 to 2, particularly preferably of 1, $R_6$, $R_7$, $R_8$, $R_9$, $R_{10}$ each independently represent H, a straight-chain, branched or cyclic $C_1$- to $C_{10}$-alkyl radical, preferably $C_1$- to $C_6$-alkyl radical, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, and/or $COOR_{11}$ where $R_{11}=C_1$- to $C_5$-alkyl radical, preferably $C_1$- to $C_3$-alkyl radical, particularly preferably $C_1$-alkyl radical.

In one embodiment d) comprises a component d.1) according to formula (I), wherein m=3, one of the radicals $R_1$, $R_2$, $R_3$, $R_4$ or $R_5$ is a $C_6$- to $C_{12}$-aryl radical, preferably $C_6$-aryl radical, or $C_2H_2Ph$ radical ("styryl") and the remaining radicals represent an H-Atom, or wherein m is an integer from 1 to 3 and $R_1$, $R_3$ and $R_5$ are identical and represent a $C_6$- to $C_{12}$-aryl radical, preferably $C_6$-aryl radical, or $C_2H_2Ph$ radical ("styryl") and $R_2$ and $R_4$ represent H.

In a further embodiment d) comprises a component d.1) according to formula (I), wherein m=3, one of the radicals $R_1$, $R_2$, $R_3$, $R_4$ or $R_5$ is a $C_6$- to $C_{12}$-aryl radical, preferably $C_6$-aryl radical, or $C_2H_2Ph$ radical ("styryl") and the remaining radicals represent an H-Atom, or wherein m is an integer from 1 to 3 and $R_1$, $R_3$ and $R_5$ represent $C_2H_2Ph$ radical ("styryl") and $R_2$ and $R_4$ represent H.

In a further embodiment d) comprises a component d.1) according to formula (I), wherein m=3, $R_3$ is a $C_6$- to $C_{12}$-aryl radical, preferably $C_6$-aryl radical, and $R_1$, $R_2$, $R_4$ and $R_5$ represent H, or wherein m is an integer from 1 to 3, $R_1$, $R_3$ and $R_5$ are identical and represent a $C_6$- to $C_{12}$-aryl radical, preferably $C_6$-aryl radical, or $C_2H_2Ph$ radical ("styryl") and $R_2$ and $R_4$ represent H.

In a further preferred embodiment d) comprises a component d.1) according to formula (I), wherein m is an integer from 1 to 3, $R_1$, $R_3$ and $R_5$ are identical and represent a $C_6$- to $C_{12}$-aryl radical, preferably $C_6$-aryl radical, or $C_2H_2Ph$ radical ("styryl") and $R_2$ and $R_4$ represent H.

In a further embodiment d) comprises a component d.1) according to formula (I), wherein m is an integer from 1 to 3, $R_1$, $R_3$ and $R_5$ are identical and represent $C_2H_2Ph$ radical ("styryl") and $R_2$ and $R_4$ represent H.

In a further embodiment the halogen-free flame retardant d) comprises a mixture of compounds d.1) according to formula (I), where m=1, m=2 and m=3, $R_1$, $R_3$ and $R_5$ are identical and represent $C_2H_2Ph$ radical ("styryl") and $R_2$, $R_4$ represent H, In a further embodiment d) comprises a component d.1) according to formula (I), wherein m is an integer from 1 to 3, $R_1$, $R_3$ and $R_5$ are identical and represent $C_2H_2Ph$ radical ("styryl") and $R_2$ and $R_4$ represent H, wherein component d.1) is in the form of a mixture of compounds where m=3 in an amount of 20 to 26 wt %, where m=2 in an amount of 25 to 35 wt % and where m=1 in an amount of 45 to 55 wt %.

In one embodiment of d.2) according to formula (II) n represents an integer from 1 to 4, preferably from 1 to 2, particularly preferably 1, represent and one of the radicals $R_6$, $R_7$, $R_8$, $R_9$ or $R_{10}$ is selected from the group consisting of H, straight-chain, branched or cyclic $C_1$- to $C_{10}$-alkyl radical, preferably $C_1$- to $C_6$-alkyl radical, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, or $COOR_{11}$ where $R_{11}=C_1$- to $C_5$-alkyl radical, preferably $C_1$- to $C_3$-alkyl radical, particularly preferably $C_1$-alkyl radical, and the remaining radicals $R_6$, $R_7$, $R_8$, $R_9$ or $R_{10}$ represent an H atom.

In a further embodiment of d.2) according to formula (II) n represents an integer from 1 to 4, preferably from 1 to 2, particularly preferably 1, one of the radicals $R_6$, $R_7$, $R_8$, $R_9$ or $R_{10}$ is selected from the group consisting of H, O-alkyl radical having $C_1$ to $C_5$-carbon atoms, preferably having $C_1$ to $C_3$-carbon atoms, particularly preferably having $C_1$-carbon atoms, or $COOR_{11}$ where $R_{11}=C_1$- to $C_5$-alkyl radical, preferably $C_1$- to $C_3$-alkyl radical, particularly preferably $C_1$-alkyl radical, and the remaining radicals $R_6$, $R_7$, $R_8$, $R_9$ or $R_{10}$ represent an H atom.

In a preferred embodiment of d.2) according to formula (II) n represents an integer from 1 to 4, preferably from 1 to 2, particularly preferably of 1, and the radicals $R_6$, $R_7$, $R_8$, $R_9$ and $R_{10}$ are identical and represent H.

In a further preferred embodiment of d.2) according to formula (II) n represents an integer of 1 and the radicals $R_6$, $R_7$, $R_8$, $R_9$ and $R_{10}$ are identical and represent H.

In one embodiment the halogen-free flame retardant d) comprises a compound d.1) according to formula (I), wherein m=3, one of the radicals $R_1$, $R_2$, $R_3$, $R_4$ or $R_5$ is a $C_6$- to $C_{12}$-aryl radical, preferably $C_6$-aryl radical, or $C_2H_2Ph$ radical ("styryl") and the remaining radicals represent an H atom, or wherein m is an integer of 1 to 3 and $R_1$, $R_3$ and $R_5$ are identical and represent a $C_6$- to $C_{12}$-aryl radical, preferably $C_6$-aryl radical, or a $C_2H_2Ph$ radical ("styryl") and $R_2$ and $R_4$ represent H, or a compound d.2) according to formula (II), in which n represents an integer from 1 to 4, preferably from 1 to 2, particularly preferably of 1, and one of the radicals $R_6$, $R_7$, $R_8$, $R_9$ or $R_{10}$ is selected from the group consisting of H, straight-chain, branched or cyclic $C_1$- to $C_{10}$-alkyl radical, preferably $C_1$- to $C_6$-alkyl radical, a $C_6$- to $C_{12}$-aryl radical, preferably $C_6$-aryl radical, a $C_2H_2Ph$ radical ("styryl"), an O-alkyl radical having $C_1$ to $C_5$-carbon atoms, preferably having $C_1$ to $C_3$-carbon atoms, particularly preferably having $C_1$-carbon atoms, an O-aryl radical having $C_6$ to $C_{12}$-carbon atoms, preferably having $C_6$-carbon atoms, or $COOR_{11}$ where $R_{11}=C_1$- to $C_5$-alkyl radical, preferably $C_1$- to $C_3$-alkyl radical, particularly preferably $C_1$-alkyl radical, and the remaining radicals $R_6$, $R_7$, $R_8$, $R_9$ or $R_{10}$ represent an H atom, employed.

In a further embodiment the halogen-free flame retardant d) comprises a compound d.1) according to formula (I), wherein m is an integer from 1 to 3, $R_1$, $R_3$ and $R_5$ are identical and represent a $C_6$- to $C_{12}$-aryl radical, preferably $C_6$-aryl radical, or $C_2H_2Ph$ radical ("styryl") and $R_2$ and $R_4$ represent H, or a compound d.2) according to formula (II), in which n represents an integer from 1 to 4, preferably from 1 to 2, particularly preferably of 1, one of the radicals $R_6$, $R_7$, $R_8$, $R_9$ or $R_{10}$ is selected from the group consisting of H, O-alkyl radical having $C_1$ bis $C_5$-carbon atoms, preferably having $C_1$ to $C_3$-carbon atoms, particularly preferably having $C_1$-carbon atoms, or $COOR_{11}$ where $R_{11}=C_1$- to $C_5$-alkyl radical, preferably $C_1$- to $C_3$-alkyl radical, particularly preferably $C_1$-alkyl radical, and the remaining radicals $R_6$, $R_7$, $R_8$, $R_9$ or $R_{10}$ represent an H atom.

In a further embodiment the halogen-free flame retardant d) comprises a compound d.1) according to formula (I), wherein m is an integer from 1 to 3, $R_1$, $R_3$ and $R_5$ are identical and represent $C_2H_2Ph$ radical ("styryl") and $R_2$, $R_4$ represent H, or a compound d.2) according to formula (II), in which n represents an integer from 1 to 4, preferably from 1 to 2, particularly preferably of 1, and the radicals $R_6$, $R_7$, $R_8$, $R_9$ or $R_{10}$ are identical and represent an H atom.

In a further embodiment the halogen-free flame retardant d) comprises a mixture of compounds d.1) according to formula (I), where m=1, m=2 and m=3, $R_1$, $R_3$ and $R_5$ are identical and represent $C_2H_2Ph$ radical ("styryl") and $R_2$, $R_4$ represent H, or a compound d.2) according to formula (II), in which n represents an integer from 1 to 4, preferably from 1 to 2, particularly preferably of 1, and the radicals $R_6$, $R_7$, $R_8$, $R_9$ or $R_{10}$ are identical and represent an H atom.

In a further embodiment the halogen-free flame retardant d) comprises a compound d.1) according to formula (I), wherein m is an integer from 1 to 3, $R_1$, $R_3$ and $R_5$ are identical and represent $C_2H_2Ph$ radical ("styryl") and $R_2$, $R_4$ represent H, and wherein component d.1) is in the form of a mixture of compounds where m=3 in an amount of 20 to 26 wt %, where m=2 in an amount of 25 to 35 wt % and where m=1 in an amount of 45 to 55 wt %, or a compound d.2) according to formula (II), in which n represents an integer from 1 to 4, preferably from 1 to 2, particularly preferably of 1, and the radicals $R_6$, $R_7$, $R_8$, $R_9$ or $R_{10}$ are identical and represent an H atom.

Component d) may be employed in an amount of 1 to 30 pphp (pphp=parts per hundred parts polyol), preferably of 5 to 25 pphp and particularly preferably of 8 to 20 pphp.

Component e)

Employed as component e) are aliphatic, cycloaliphatic, araliphatic, aromatic and heterocyclic di- or polyisocyanates, such as are described for example by W. Siefken in Justus Liebigs Annalen der Chemie, 562, pages 75 to 136, for example those of the formula (III)

$$Q(NCO)_n \qquad (III)$$

in which
n=2-4, preferably 2-3,
and
Q represents an aliphatic hydrocarbon radical having 2-18, preferably 6-10, carbon atoms, a cycloaliphatic hydrocarbon radical having 4-15, preferably 6-13, carbon atoms or an araliphatic hydrocarbon radical having 8-15, preferably 8-13, carbon atoms.

The polyisocyanates are for example those described in EP-A 0 007 502, pages 7-8. Particular preference is generally given to the readily industrially obtainable polyisocyanates, for example 2,4- and 2,6-tolylene diisocyanate and any desired mixtures of these isomers ("TDI"); polyphenylpolymethylene polyisocyanates as prepared by aniline-formaldehyde condensation and subsequent phosgenation ("crude MDI"), and polyisocyanates having carbodiimide groups, urethane groups, allophanate groups, isocyanurate groups, urea groups or biuret groups ("modified polyisocyanates"), especially those modified polyisocyanates which derive from 2,4- and/or 2,6-tolylene diisocyanate or from 4,4'- and/or 2,4'-diphenylmethane diisocyanate. It is preferable when at least one compound selected from the group consisting of 2,4- and 2,6-tolylene diisocyanate, 4,4'- and 2,4'- and 2,2'-diphenylmethane diisocyanate and polyphenyl polymethylene polyisocyanate ("polycyclic MDI") is employed as component e). It is particularly preferable when an isomer mixture of 2,4- and 2,6-tolylene diisocyanate is employed as component e). Particularly preferably employed as component e) is an isomer mixture of 2,4- and 2,6-tolylene diisocyanate in a weight ratio 80:20.

The NCO content of employed component e) may be in the range of 15-54%, preferably of 28-51% and particularly preferably of 47-49%.

To produce the polyurethane foams, the reaction components are reacted by the one-step process known per se, often using mechanical means, for example those described in EP-A 355 000. Details of processing means also contemplated in accordance with the invention are reported in Kunststoff-Handbuch, volume VII, edited by Vieweg and Höchtlen, Carl-Hanser-Verlag, Munich 1993, for example on pages 139 to 265.

The index indicates the percentage ratio of the actually employed isocyanate amount to the stoichiometric, i.e. calculated for the conversion of the OH equivalents, amount of isocyanate groups (NCO) amount.

Index=[(isocyanate amount employed):(isocyanate amount calculated)]·100 (VIII)

In one embodiment the reaction of the isocyanate-reactive components A with the isocyanate component B is effected with an index of 50 to 250, preferably with an index of 90-125.

The polyurethane foams produced by the process according to the invention are preferably flexible polyurethane foams. These feature not only flame retardant properties but also low emission characteristics. Thus, the fogging value according to DIN 75201 B of the polyurethane foams produced according to the invention is ≤0.70 mg. The overall sum of the omissions according to VDA 278 (VOC value+FOG value) is ≤1250 mg/kg.

The polyurethane foams produced according to the invention may be employed inter alia in the construction, automobile and/or furniture industries.

EXAMPLES d-1: tris(phenoxyethyl) phosphate
d-2: tris(tristyrylphenyl) phosphate
d-3: Fyrol® PCF from ICL Industrial Products: tris(2-chloroisopropyl) phosphate
d-4: Phosflex® 71B from ICL Industrial Products: mixture of butylated triphenylphosphate ester
Polyether polyol a-1: DMC-catalyzed, glycerol- (90.2%) and monopropylene-glycol-started (9.8%) polyether polyol comprising 99% propylene oxide and 1% ethylene oxide, having an OH number of 56 mg KOH/g.
c-1: Niax® L620 from Momentive Performance Chemicals, Germany (catalyst)
c-2: Dabco® 33LV from Air Products, Germany (catalyst)

c-3: Niax® A1 from Momentive Performance Chemicals, Germany (catalyst)

c-4: Dabco® T-9 (Tin (II) 2-ethylhexanoate) from Air Products, Germany (catalyst)

e-1: Mixture of 2,4- and 2,6-TDI in a weight ratio of 80:20 and having an NCO content of 48 wt %.

The phosphoric esters d-1, and d-2 were produced as follows:

d-1: tris(phenoxyethyl) phosphate

Under a dry nitrogen atmosphere, 477.00 g of phenoxyethanol (3.45 mol) in 4.6 l of dry toluene are initially charged into a 10 l four-necked flask stirring apparatus and heated to 80° C. 621.00 g of sodium methoxide solution (~30 wt % in methanol; 3.45 mol) are added dropwise via a dropping funnel and the dropping funnel is then rinsed out with 20 g of dry methanol. 3.8 l of methanol/toluene are distilled off via a distillation bridge up to a tops temperature of 110° C. Two 1 l portions of dry toluene are further metered in during the distillation. After cooling of the reaction mixture to 90° C. a further 500 mL of dry toluene are metered in and a solution of 176.53 g of phosphoryl chloride (1.15 mol) in 400 mL of dry toluene are added dropwise. The reaction is allowed to react for 4.5 h under reflux and then cool to room temperature. The obtained solution is filtered off from the precipitated solid, divided among two separating funnels and in each case extracted four times with 400 mL of water. Concentrating at 50° C. under vacuum affords 278.0 g (53% of theory) of the high-viscosity target compound from the combined toluene solutions.

$^{31}$P{$^1$H} NMR (toluene, 25° C.): −2.0 ppm [s]

d-2: tris(tristyrylphenyl) phosphate

Under a dry nitrogen atmosphere, 669.20 g of tristyrylphenol (1.8 mol) in 4 l of dry toluene are initially charged into a 10 l four-necked flask stirring apparatus and heated to 80° C. 324.00 g of sodium methoxide solution (~30 wt % in methanol; 1.8 mol) are added dropwise via a dropping funnel and the dropping funnel is then rinsed out with 20 g of dry methanol. 2.1 l of methanol/toluene are distilled off via a distillation bridge up to a tops temperature of 110° C. After cooling of the reaction mixture to 80° C. a further 1 lL of dry toluene is metered in and a solution of 92.10 g of phosphoryl chloride (0.6 mol) in 500 mL of dry toluene are added dropwise. The reaction is allowed to react for 1.5 h under reflux and then cool to room temperature. The obtained solution is filtered off from the precipitated solid and in a separating funnel extracted with 100 mL of 1 M HCl and subsequently four times with 200 mL of water. Concentrating at 50° C. under vacuum affords 446.6 g (64% of theory) of a high-viscosity residue. The residue comprises about 23% tris(tristyrylphenyl) phosphate, about 28% bis(tristyrylphenyl) phosphate and about 49% mono(tristyrylphenyl) phosphate. $^{31}$P{$^1$H} NMR (toluene, 25° C.): −5.1 ppm [m, mono(tristyrylphenyl) phosphate]; −7.6 ppm [m, bis(tristyrylphenyl) phosphate]; −14.8 ppm [m, tris(tristyrylphenyl)phosphate]

Tristyrylphenol: produced by Tanatex Chemicals; mixture of about 70% 2,4,6-tristyrylphenol, about 25% 2,6-distyrylphenol and tetrastyrylphenol.

The starting components according to table 1 are processed in a single-stage process by slabstock foaming under the processing conditions customary for the production of polyurethane foams. Indications concerning the input materials (pphp) are based on 100 parts of polyether polyol b-1. Table 1 reports the index for the processing stage (this determines the amount of component B to be employed relative to component A). The index (isocyanate index) indicates the percentage ratio of the actually employed isocyanate amount to the stoichiometric, i.e. calculated, isocyanate groups (NCO) amount.

$$\text{Index} = [(\text{isocyanate amount employed}):(\text{isocyanate amount calculated})] \cdot 100 \qquad (IV)$$

Apparent density was determined according to DIN EN ISO 3386-1-98.

Indentation hardness (CLD 40%) was determined according to DIN EN ISO 3386-1-98 at 40% deformation, 4th cycle.

Fogging was determined by gravimetric means according to DIN 75201B.

The VOC value (Volatile Organic Compounds) in mg/kg (toluene equivalent) and FOG value in mg/kg (hexadecane equivalent) was determined according to VDA 278 (October 2011).

The fire test was performed according to Directive 95/28/EC.

$^{31}$P{$^1$H} NMR was measured in toluene with 85% aqueous phosphoric acid as external standard on a Bruker DPX 400 spectrometer at 25° C.

|  | Unit | Example 1 | Example 2 | Example 3 (comp.) | Example 4 (comp.) | Example 5 (comp.) |
| --- | --- | --- | --- | --- | --- | --- |
| a-1 | pphp | 100 | 100 | 100 | 100 | 100 |
| Water | pphp | 3.5 | 3.5 | 3.5 | 3.5 | 3.5 |
| d-1 | pphp | 8.0 | | | | |
| d-2 | pphp | | 8.0 | | | |
| d-3 | pphp | | | 8.0 | | |
| d-4 | | | | | | 8.0 |
| c-1 | pphp | 0.30 | 0.30 | 0.30 | 0.30 | 0.30 |
| c-2 | pphp | 0.24 | 0.24 | 0.24 | 0.24 | 0.24 |
| c-3 | pphp | 0.04 | 0.04 | 0.04 | 0.04 | 0.04 |
| c-4 | pphp | 0.22 | 0.22 | 0.22 | 0.22 | 0.22 |
| Index |  | 102 | 102 | 102 | 102 | 102 |
| e-1 | pphp | 43.54 | 43.54 | 43.54 | 43.54 | 43.54 |
| Apparent density | kg/m$^3$ | 33.2 | 26.7 | 36.2 | 33.0 | 35.7 |
| Indentation hardness | kPa | 3.9 | 2.5 | 4.04 | 4.6 | 4.2 |
| Fogging DIN75201B | mg | 0.29 | 0.56 | 22.6 | 0.04 | 0.72 |
| VOC value (VDA278) | mg/kg | 412 | 542 | 1256 | 160 | 496 |
| FOG value (VDA278) | mg/kg | 99 | 632 | 3931 | 2 | 829 |
| Sum of VOC + FOG values | mg/kg | 511 | 1174 | 5187 | 162 | 1325 |
| Directive 95/28/EC fire test | passed | yes | yes | yes | no | yes |

(comp.): Comparison

The inventive examples 1 and 2 exhibit markedly lower fogging values (gravimetric) compared to polyurethane foams produced with the conventional halogen-containing flame retardants (comparative example 3) or with butylated triphenylphosphate ester as flame retardant (comparative example 5).

Moreover, the polyurethane foams produced with the flame retardants according to the invention exhibit markedly fewer emissions of high- and low-volatility organic constituents (sum of VOC and FOG value according to VDA 278).

The invention claimed is:

1. A flame-retarded polyurethane foam obtainable by reacting a reaction mixture comprising a component which comprises
   a) at least one compound which comprises isocyanate-reactive hydrogen atoms,
   b) water and/or a physical blowing agent,
   c) auxiliary and additive substances,
   d) at least one halogen-free flame retardant comprising
      d.2) a phosphoric ester of formula (II)

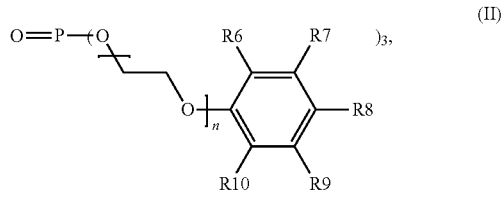

(II)

wherein:

n represents an integer from 1 to 4, $R_6$, $R_7$, $R_8$, $R_9$, $R_{10}$ each independently represent a hydrogen atom, a straight-chain, branched or cyclic $C_1$- to $C_{10}$-alkyl radical, a $C_6$- to $C_{12}$-aryl radical, a $C_2H_2Ph$ radical, an O-alkyl radical having $C_1$ to $C_5$-carbon atoms, an O-aryl radical having $C_6$ to $C_{12}$-carbon atoms and/or $COOR_{11}$ wherein $R_{11}$ represents a $C_1$- to $C_5$-alkyl radical, with e) at least one di- and/or polyisocyanate, to form a foam, wherein the reaction mixture is free from halogen-containing flame retardants.

2. The flame-retarded polyurethane foam as claimed in claim 1, wherein the polyurethane foam is a flexible polyurethane foam.

3. An article comprising the polyurethane foam as claimed in claim 1 in the automobile, construction and/or furniture industries.

4. The article of claim 3, wherein said article comprises an automobile part, a construction part or a furniture part.

* * * * *